(12) United States Patent
Fanelli et al.

(10) Patent No.: US 12,082,811 B2
(45) Date of Patent: Sep. 10, 2024

(54) SURGICAL STAPLER ANVIL JAW WITH VARIABLE FIRING MEMBER SLOT

(71) Applicant: Cilag GmbH International, Zug (CH)

(72) Inventors: Nicholas Fanelli, Morrow, OH (US); Geoffrey C. Hueil, Mason, OH (US); Gary S. Jaworek, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/702,877

(22) Filed: Mar. 24, 2022

(65) Prior Publication Data
US 2023/0301653 A1 Sep. 28, 2023

(51) Int. Cl.
*A61B 17/072* (2006.01)
*A61B 17/068* (2006.01)

(52) U.S. Cl.
CPC .... *A61B 17/07207* (2013.01); *A61B 17/0686* (2013.01); *A61B 2017/07257* (2013.01)

(58) Field of Classification Search
CPC .......... A61B 17/07207; A61B 17/0686; A61B 2017/07257
See application file for complete search history.

(56) References Cited

U.S. PATENT DOCUMENTS

| | | | |
|---|---|---|---|
| 5,632,432 A * | 5/1997 | Schulze | A61B 17/07207 227/176.1 |
| 7,380,696 B2 | 6/2008 | Shelton, IV et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 9,186,142 B2 | 11/2015 | Fanelli et al. | |
| 9,517,065 B2 | 12/2016 | Simms et al. | |
| 9,597,078 B2 * | 3/2017 | Scirica | A61B 17/07207 |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |

(Continued)

FOREIGN PATENT DOCUMENTS

| | | |
|---|---|---|
| EP | 2644114 A2 | 10/2013 |
| EP | 3338702 A1 | 6/2018 |
| EP | 3420959 A2 | 1/2019 |

OTHER PUBLICATIONS

International Search Report and Written Opinion dated Aug. 2, 2023 for Application No. PCT/IB2023/052752, 15 pgs.

*Primary Examiner* — Robert F Long
*Assistant Examiner* — Eduardo R Ferrero
(74) *Attorney, Agent, or Firm* — Frost Brown Todd LLP

(57) ABSTRACT

An apparatus includes a jaw body configured to couple with an end effector portion of a surgical stapler and cooperate with an opposing jaw to compress, staple, and cut tissue. An anvil surface of the jaw body has a plurality of staple forming pockets configured to form a plurality of staples. An elongate slot extends through the anvil surface from a proximal slot end at a proximal end of the staple forming pockets to a distal slot end at a distal end of the staple forming pockets. A first slot portion is configured to slidably receive a first portion of a firing member, and a second slot portion opens to the anvil surface and is configured to slidably receive a second portion of the firing member. A dimension of the second slot portion varies along the longitudinal axis between the proximal slot end and the distal slot end.

20 Claims, 19 Drawing Sheets

(56) References Cited

U.S. PATENT DOCUMENTS

| | | | |
|---|---|---|---|
| 9,839,421 B2 | 12/2017 | Zerkle et al. | |
| 10,092,292 B2 | 10/2018 | Boudreaux et al. | |
| 2008/0082124 A1* | 4/2008 | Hess | A61B 17/115 |
| | | | 606/219 |
| 2012/0080503 A1* | 4/2012 | Woodard, Jr. | A61B 17/0643 |
| | | | 227/181.1 |
| 2012/0181322 A1* | 7/2012 | Whitman | A61B 17/068 |
| | | | 227/176.1 |
| 2012/0193396 A1* | 8/2012 | Zemlok | A61B 17/07207 |
| | | | 227/176.1 |
| 2012/0228358 A1* | 9/2012 | Zemlok | A61B 17/07207 |
| | | | 227/176.1 |
| 2013/0075445 A1* | 3/2013 | Balek | A61B 17/07207 |
| | | | 227/176.1 |
| 2013/0256375 A1* | 10/2013 | Shelton, IV | A61B 17/0643 |
| | | | 227/176.1 |
| 2014/0005679 A1* | 1/2014 | Shelton, IV | A61B 17/07207 |
| | | | 606/130 |
| 2014/0239043 A1* | 8/2014 | Simms | A61B 17/07207 |
| | | | 227/176.1 |
| 2014/0284372 A1* | 9/2014 | Kostrzewski | A61B 17/07207 |
| | | | 227/176.1 |
| 2016/0345971 A1* | 12/2016 | Bucciaglia | A61B 17/07207 |
| 2017/0296191 A1* | 10/2017 | Shelton, IV | A61B 17/07207 |
| 2018/0168611 A1* | 6/2018 | Shelton, IV | A61B 17/0644 |
| 2018/0168616 A1* | 6/2018 | Shelton, IV | A61B 34/30 |
| 2018/0235610 A1* | 8/2018 | Harris | A61B 17/072 |
| 2018/0310935 A1* | 11/2018 | Wixey | A61B 17/00234 |
| 2018/0353179 A1* | 12/2018 | Shelton, IV | A61B 17/068 |
| 2018/0368839 A1* | 12/2018 | Shelton, IV | A61B 17/07207 |
| 2019/0290267 A1* | 9/2019 | Baxter, III | A61B 17/00491 |

* cited by examiner

SURGICAL STAPLER ANVIL JAW WITH VARIABLE FIRING MEMBER SLOT

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
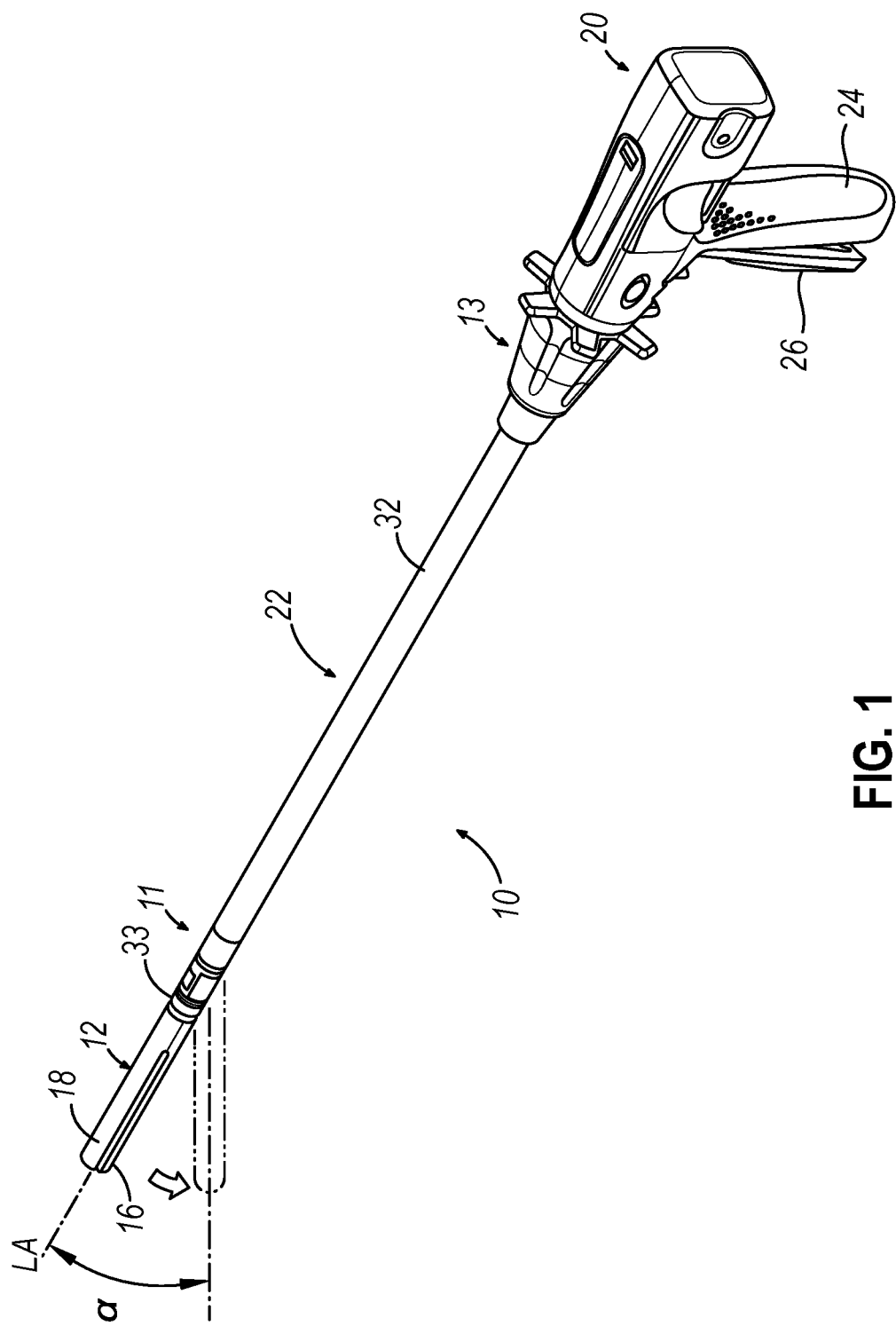
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) (also referred to herein as a cartridge jaw) that includes a staple cartridge (37), and an upper jaw in the form of a pivotable anvil (18) (also referred to herein as an anvil jaw).

Handle portion (20) includes a pistol grip (24) and a closure trigger (26). Closure trigger (26) is pivotable toward pistol grip (24) to cause clamping, or closing, of anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
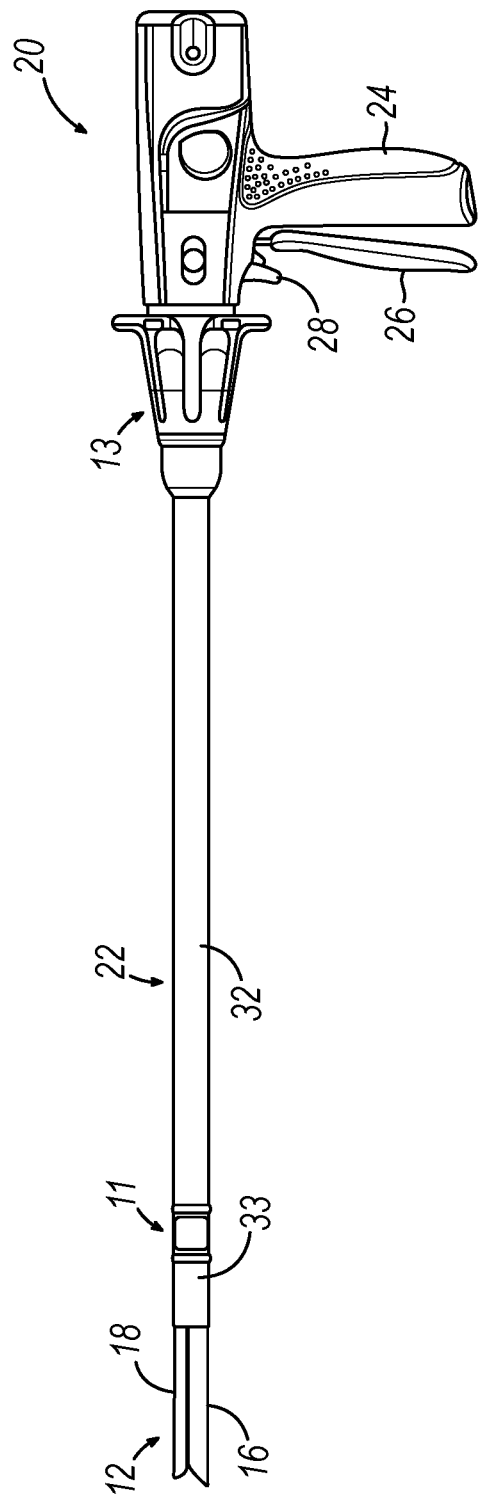
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B1) that is formed through lower jaw (16). Middle pin (46) slidingly engages a top surface of lower jaw (16), cooperating with firing beam cap (44).

Figure 3:
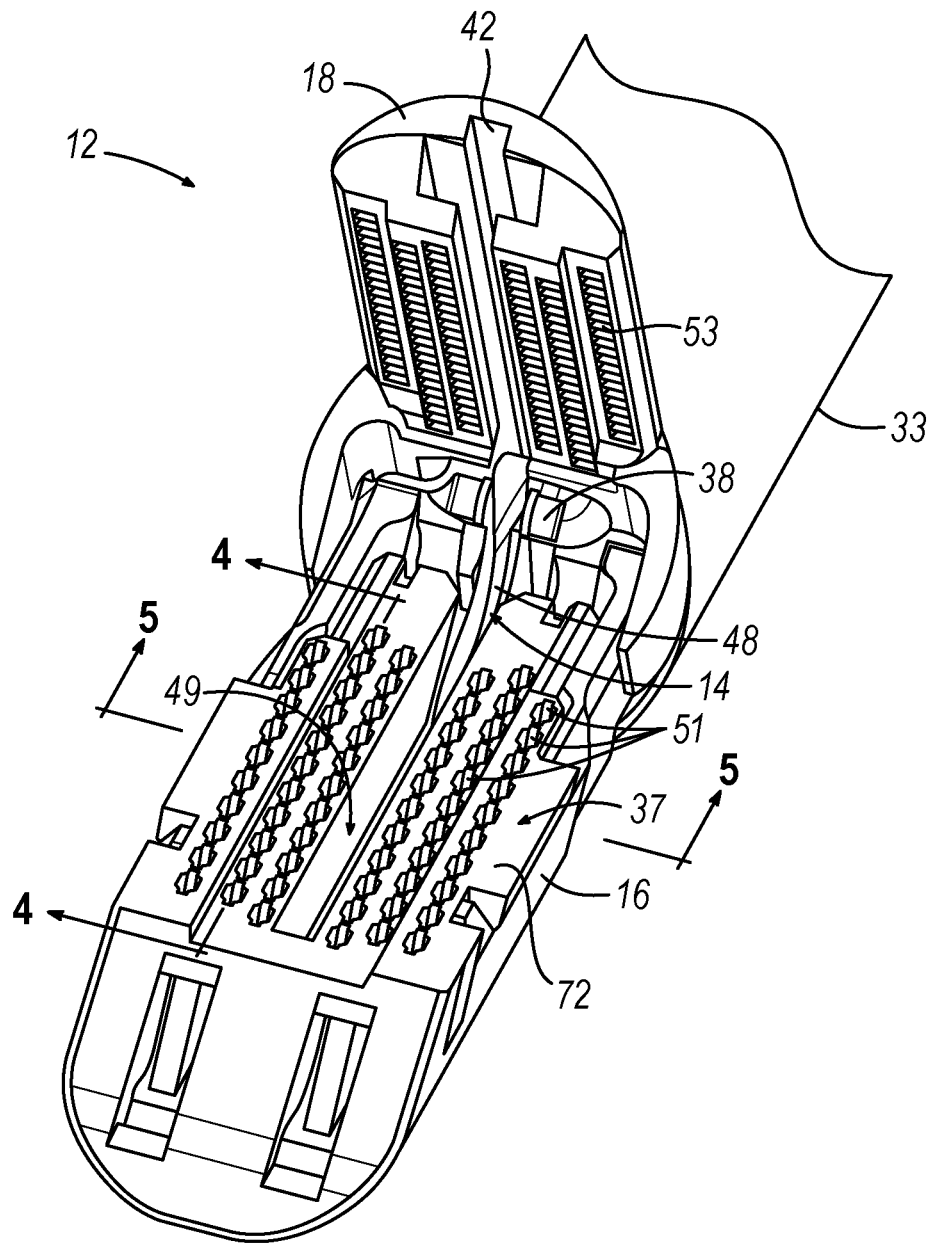
FIG. 3 depicts a perspective view of an end effector of the instrument of FIG. 1 in an open state.
Figure 4A:
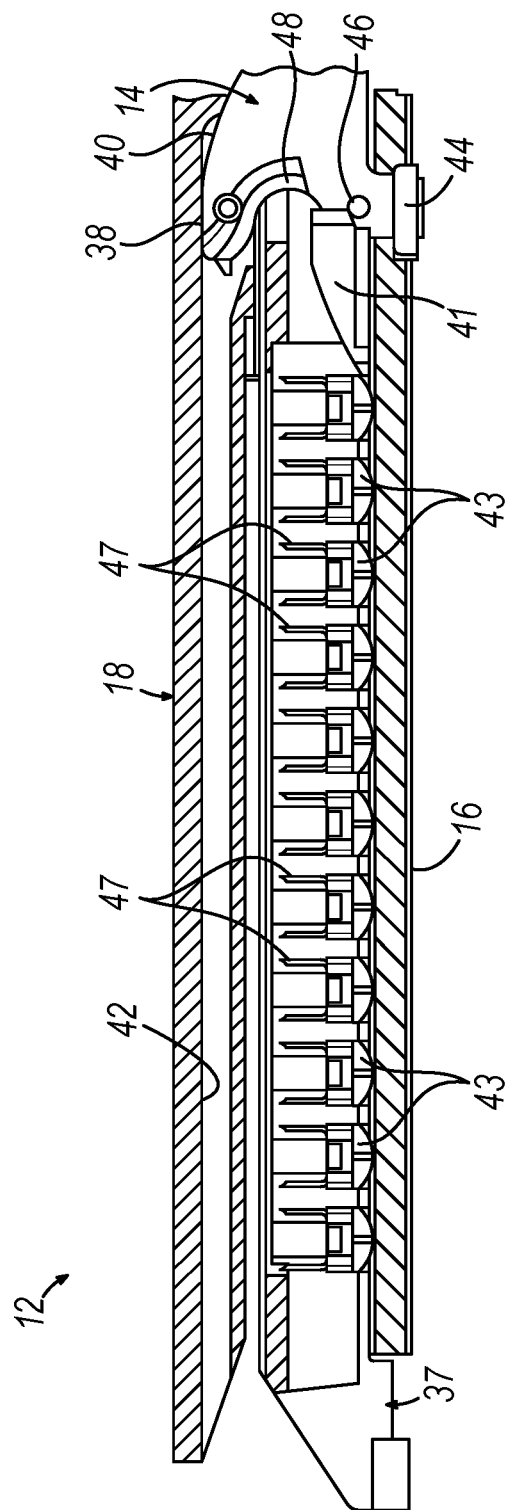
FIG. 4A depicts a side cross-sectional view of the end effector of FIG. 3, taken along line 4-4 of FIG. 3, with a firing beam in a proximal position.
Figure 4B:
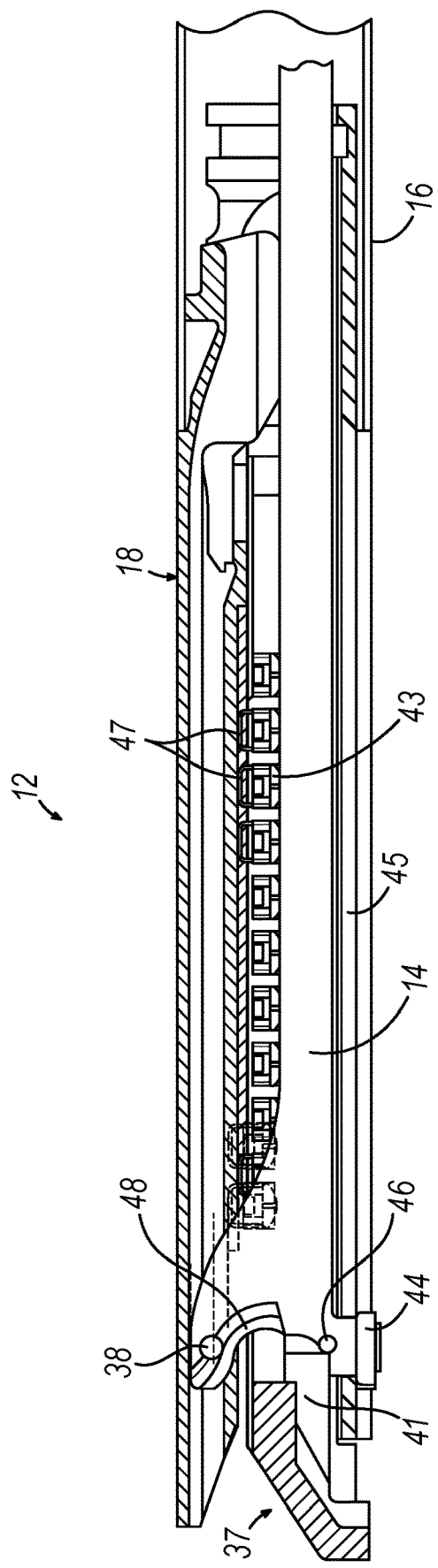
FIG. 4B depicts a side cross-sectional view of the end effector of FIG. 3, taken along line 4-4 of FIG. 3, with the firing beam in a distal position.
Figure 5:
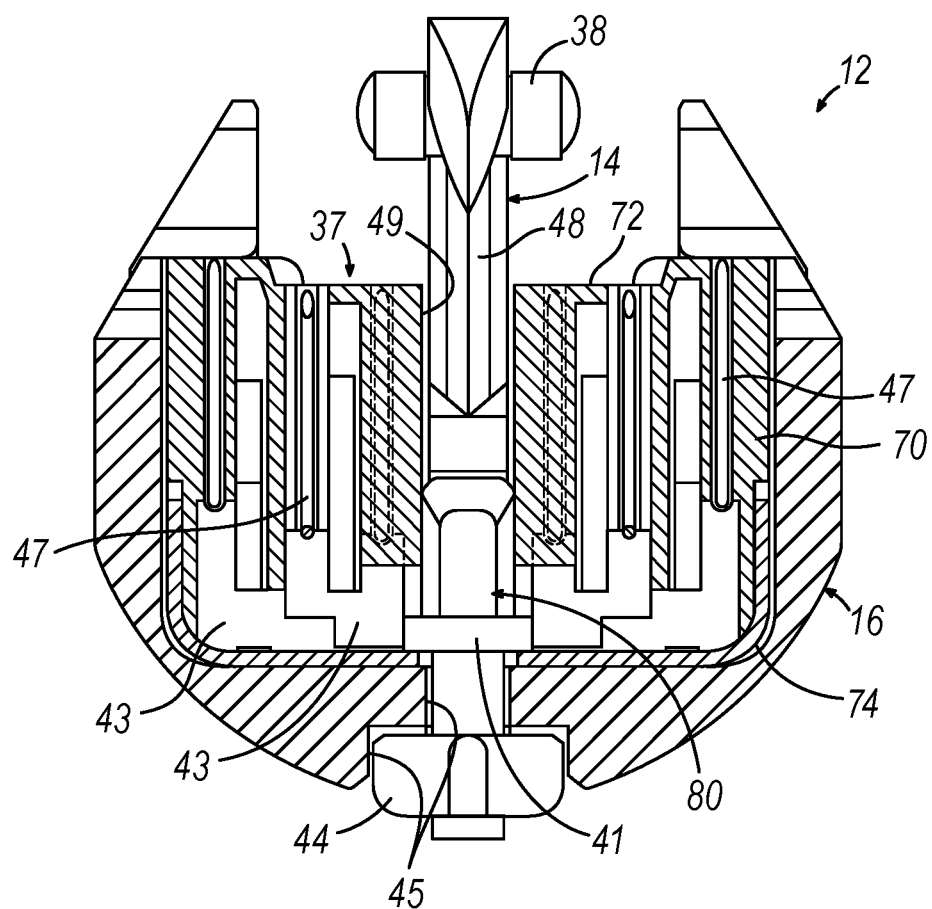
FIG. 5 depicts an end cross-sectional view of the end effector of FIG. 3, taken along line 5-5 of FIG. 3.
Figure 6:
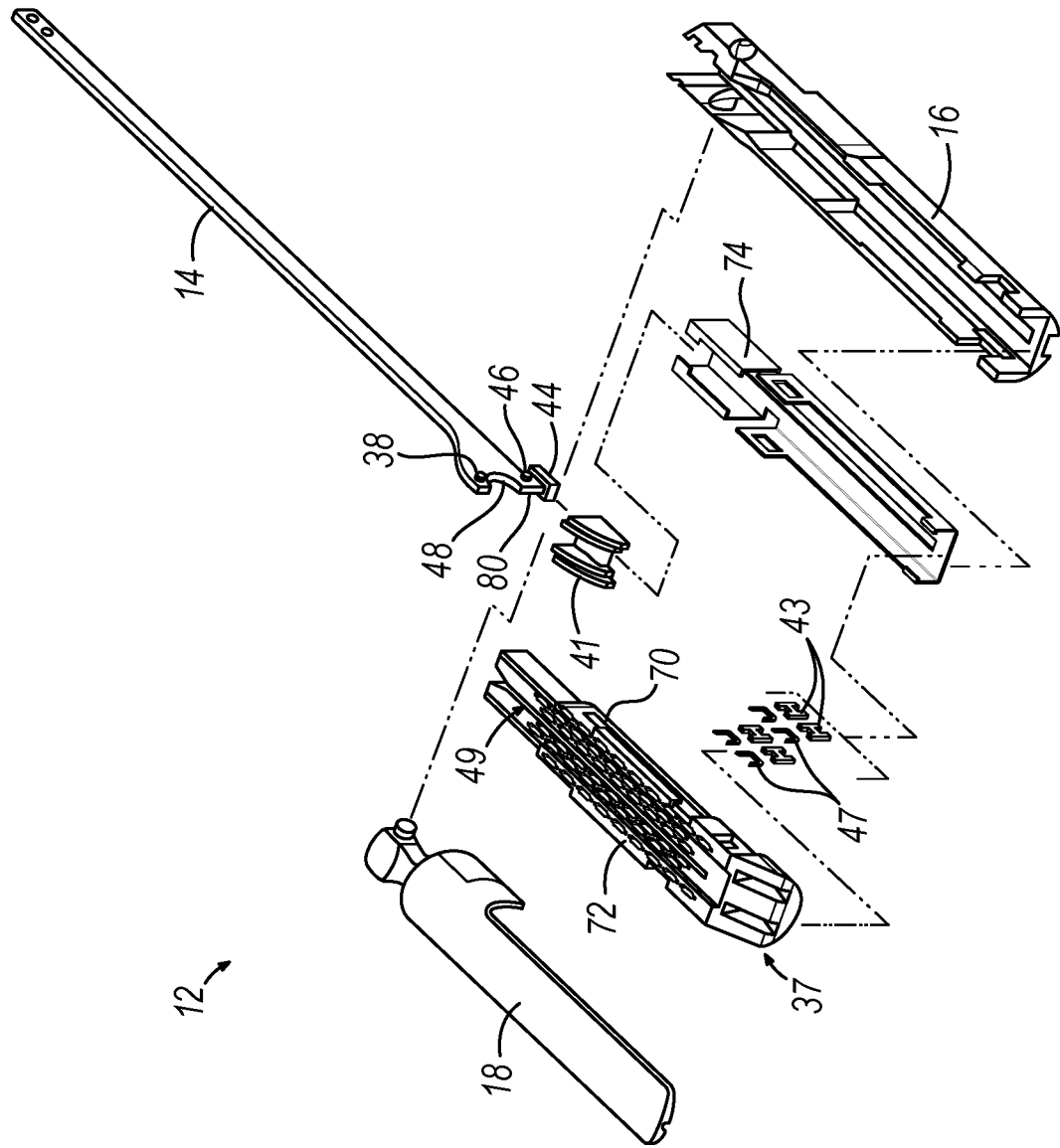
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), a firing member in the form of firing beam (14) is then advanced distally into engagement with anvil (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
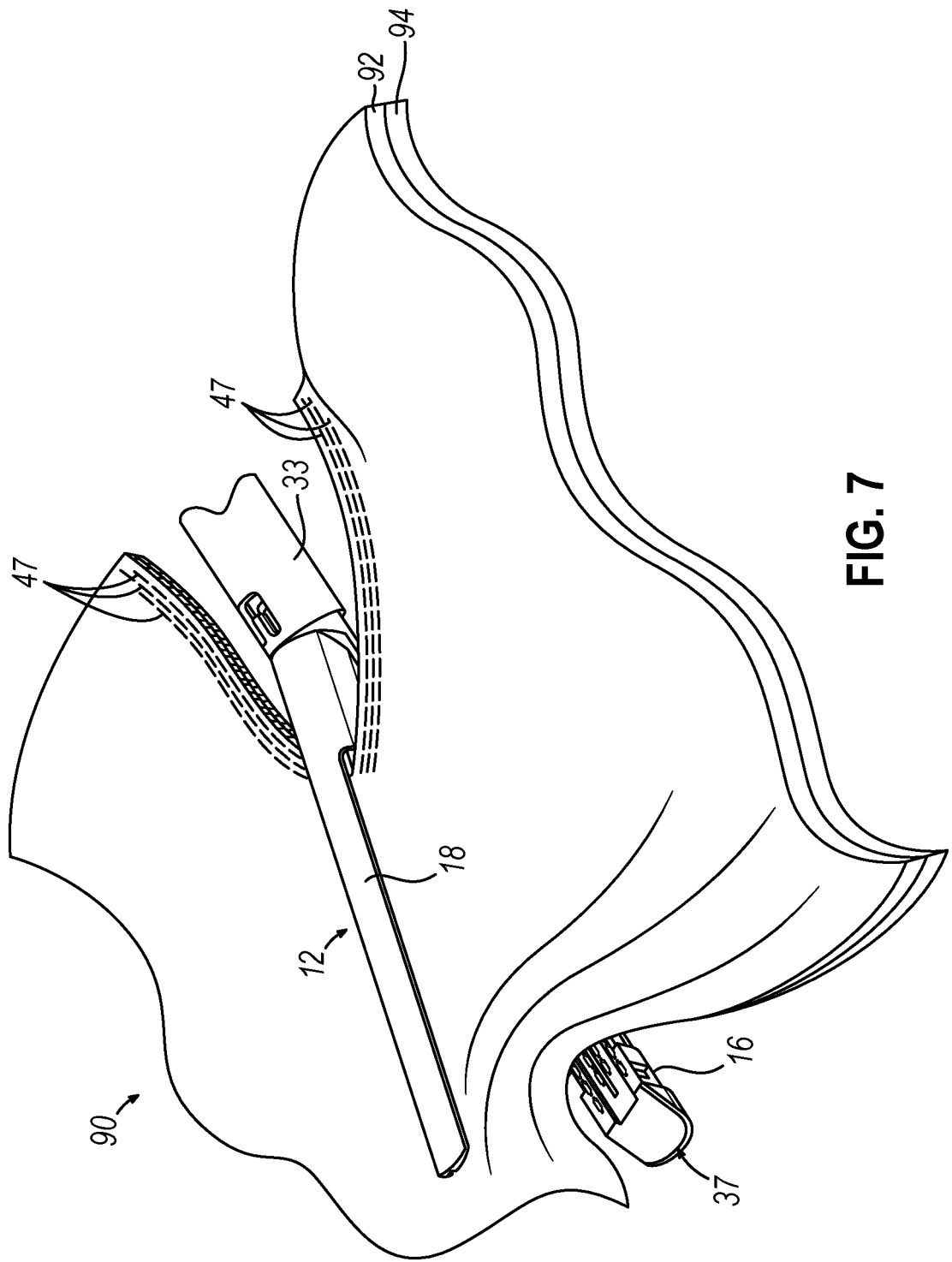
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Alternative Anvil Jaws Having Two-Piece Construction

As described above, in response to actuation of firing trigger (28) by an operator, firing beam (14) actuates distally through end effector (12) such that upper pin (38) advances distally through anvil slot (42) of anvil jaw (18). More specifically, upper pin (38) rides distally along a pair of elongate inner guide surfaces of anvil jaw (18) defined by a pair of flanges that are spaced apart to define anvil slot (42), as seen best in FIGS. 3-4B. This engagement between upper pin (38) and the inner guide surfaces of anvil slot (42) constrains anvil jaw (18) vertically relative to cartridge jaw (16) during firing on tissue.

In some instances, it may be desirable to alternatively shape these flanges and corresponding inner guide surfaces of anvil jaw (18) to have a predetermined effect during firing on the size of a tissue gap defined between the stapling surfaces of anvil jaw (18) and cartridge jaw (16) to control a height of formed staples (47). To that end, a section of tissue (90) being fired upon by end effector (12) may have a variable thickness along its length, thus warranting that staples (47) be formed with varying heights along the length of end effector (12) to properly seal that section of tissue (90). It may also be desirable to alternatively shape the flanges of anvil jaw to promote more effective lateral alignment of anvil jaw (18) with cartridge jaw (16) and thereby facilitate proper formation of staples (47). To that end, proper lateral alignment of end effector jaws (16, 18) ensures alignment of staple apertures (51) of staple cartridge (37) with the respective staple forming pockets (53) of anvil jaw (18), thus ensuring proper formation of staples (47) by staple forming pockets (53) as staples (47) are deployed from staple apertures (51).

A. Exemplary Anvil Jaw with Level Firing Member Guide Features

Figure 8:
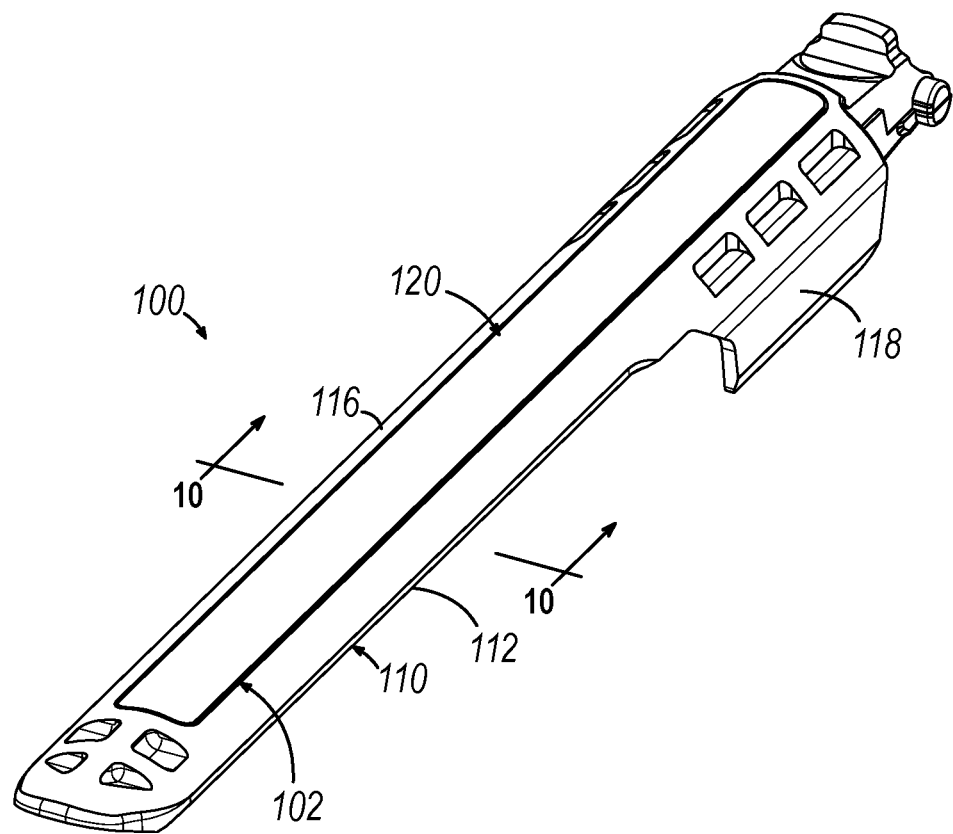
FIG. 8 depicts a perspective view of another exemplary anvil jaw configured for use with the end effector of FIG. 3.
Figure 9:
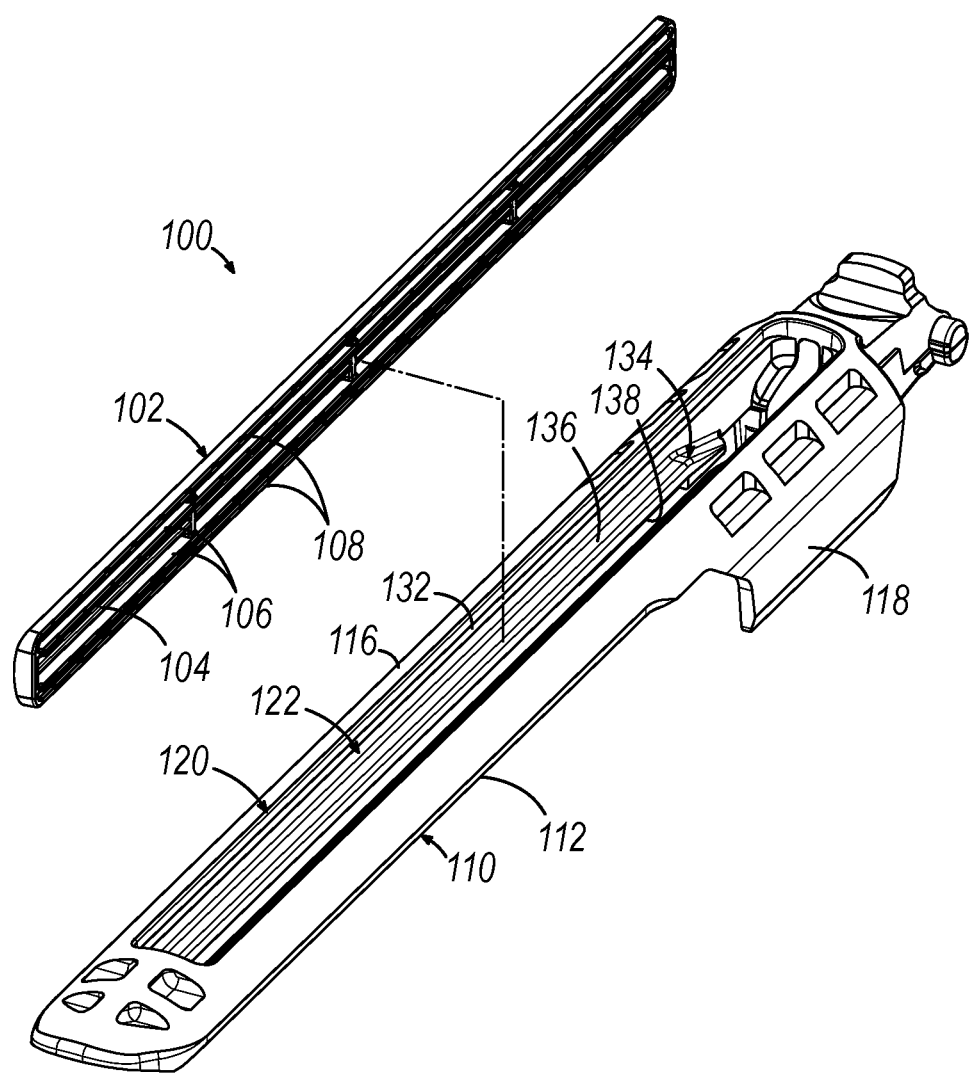
FIG. 9 depicts a disassembled perspective view of the anvil jaw of FIG. 8, showing an anvil jaw cap and an anvil jaw body of the anvil jaw separated to reveal an elongate opening and an elongate firing member slot of the anvil jaw body.

FIGS. 8 and 9 show an exemplary alternative anvil jaw (100) that is configured for use with end effector (12) in place of anvil jaw (18) and is similar to anvil jaw (18) as described above except as otherwise described below. Whereas anvil jaw (18) is manufactured as a single unitary structure, anvil jaw (100) of the present example includes an anvil jaw body (110) and an anvil jaw cap (102) secured to the upper portion of anvil jaw body (110), such that anvil jaw body (110) and anvil jaw cap (102) may be manufactured separately as distinct components, for example via liquid metal molding, and then joined together, for example via welding. As described in greater detail below in connection with the alternative anvil jaw bodies (210, 310, 410, 510, 610 710) shown in FIGS. 12-17, such a two-piece construction of anvil jaw (100) enables the firing member guide features of anvil jaw body (110) to be formed with a selected geometry, for example where one or more dimensions of such firing member guide features vary along the length of anvil jaw (100).

Anvil jaw cap (102) is configured to enclose an anvil slot (122) of anvil jaw body (110), as described below, and a firing member, such as firing beam (14), slidably disposed within anvil slot (122). An underside of anvil jaw cap (102) includes a plurality of elongate rails that extend downwardly and are configured to support anvil jaw cap (102) relative to anvil jaw body (110), as well as stabilize a distal portion of firing beam (14) within anvil slot (122), as described in greater detail below. In the present example, anvil jaw cap (102) includes a central rail (104), a pair of inner rails (106) spaced outwardly from central rail (104), and a pair of outer rails (108) spaced outwardly from inner rails (106). Anvil jaw cap (102) can be permanently or removably affixed to the anvil jaw body (110). By way of example only, anvil cap (102) may be affixed to the anvil body (110) by use of an adhesive, laser welding, a mechanical locking mechanism, or by any other suitable means readily apparent to those of ordinary skill in the art in view of the teachings herein. Anvil jaw cap (102) may be produced from the same material as anvil body (110) or from any other material readily apparent to those of ordinary skill in the art in view of the teachings herein.

Figure 10:
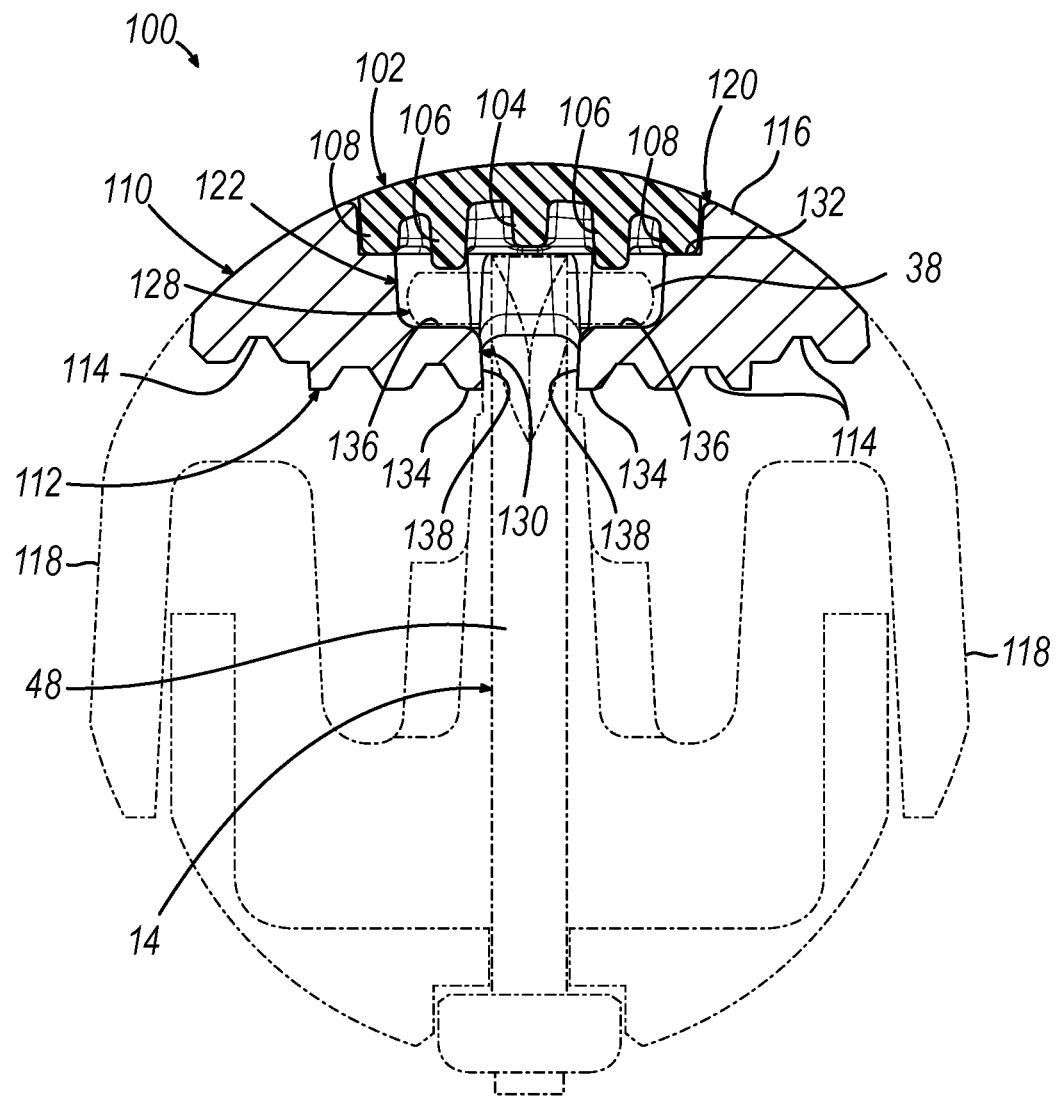
FIG. 10 depicts a cross-sectional end view of the anvil jaw of FIG. 8, taken along line 10-10 in FIG. 8, showing a proximal end of the anvil jaw body and a firing member of the end effector of FIG. 3 in broken lines for added clarity.
Figure 11:
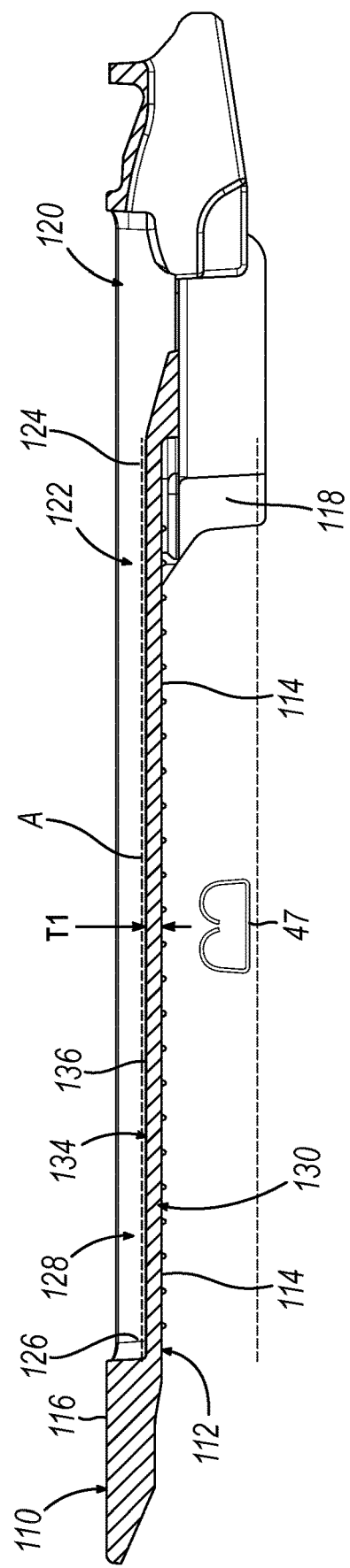
FIG. 11 depicts a cross-sectional side view of the anvil jaw body of FIG. 8, showing a firing member slot flange of the anvil jaw body having a constant thickness that defines a level flange surface, and schematically showing an exemplary staple formable by the anvil jaw body.

As shown best in FIGS. 9-11, anvil jaw body (110) includes an interior side that defines an anvil surface (112) configured to compress tissue and having a plurality of staple forming pockets (114), and an opposed exterior side defining an exterior surface (116). Anvil jaw body (110) may also include a pair of tissue stops (118) that extend downwardly from a proximal portion of anvil jaw body (110) on opposed lateral sides such that tissue stops (118) extend beyond anvil surface (112). Tissue stops (118) are configured to inhibit tissue (90) from advancing too far proximally relative to anvil jaw (100) when tissue (90) is positioned between anvil jaw (100) and cartridge jaw (16). More specifically, tissue stops (118) allow tissue (90) to be proximally advanced in end effector (12) only to a predetermined position to ensure adequate engagement of staples (47) with tissue (90) and to ensure that anvil jaw (100) can pivot to a closed state without binding on tissue (90). Tissue stops (118) are also configured to limit the lateral rotation of anvil jaw (100) relative to lower cartridge jaw (16) by engaging lateral side portions of lower cartridge jaw (16). This can be useful for ensuring proper lateral alignment between the more proximally located staples (47) and the corresponding staple forming pockets (114).

Anvil jaw body (110) further includes an elongate opening (120) in exterior surface (116), and an elongate anvil slot (122) (also referred to herein as a firing member slot) that extends through anvil surface (112) and communicates with elongate opening (120). Elongate opening (120) is sized and shaped to receive anvil jaw cap (102) to thereby enclose anvil slot (122). As shown in FIG. 11, anvil slot (122) extends along a longitudinal axis (A) of anvil jaw (100) from a proximal slot end (124) defined at a proximal end of the plurality of staple forming pockets (114), to a distal slot end (126) defined at a distal end of the plurality of staple forming pockets (114). As shown best in FIG. 10, anvil slot (122) includes a wide slot portion (128) and a narrow slot portion (130), with wide slot portion (128) being wider than narrow slot portion (130) in a direction transverse to the longitudinal axis (A) of anvil jaw (100). Wide slot portion (128) is located above narrow slot portion (130) such that wide slot portion (128) opens directly to elongate opening (120) in exterior surface (116) and narrow slot portion (130) opens directly to anvil surface (112). Additionally, wide slot portion (128) is enclosed by anvil jaw cap (102) when cap (102) is secured to anvil jaw body (110). As shown, anvil jaw cap (102) is positioned within elongate opening (120) such that outer rails (108) are seated on respective recessed rim surfaces (132) of anvil jaw body (110).

Both wide slot portion (128) and the narrow slot portion (130) extend the length of anvil slot (122) between proximal slot end (124) and distal slot end (126) and cooperate to control the size of a tissue gap between anvil surface (112) of anvil jaw (100) and upper deck (72) of staple cartridge (37) as end effector (12) is fired on clamped tissue. To that end, anvil slot (122) defines a pair of elongate firing member guide features in the form of flanges (134) that are spaced apart from one another by narrow slot portion (130) and extend along the length of anvil slot (122), with flanges (134) being configured cooperate to guide the distal portion of firing beam (14) longitudinally through anvil slot (122). In particular, wide slot portion (128) is configured to slidably receive and guide upper pin (38) along upper guide surfaces (136) of flanges (134), while narrow slot portion (130) is configured to slidably receive and guide cutting edge (48) between confronting side guide surfaces (138) of flanges (134). Additionally, as shown in FIG. 10, central rail (104) of anvil jaw cap (102) confronts a top surface of the cutting portion of firing beam (14) and inner rails (106) of anvil jaw cap (102) confront top surfaces of upper pin (38), such that anvil jaw cap (102) is configured to vertically constrain firing beam (14) relative to anvil slot (122).

It will be understood that when firing on clamped tissue with end effector (12) in a closed state, the clamped tissue may exert a reactionary force on anvil surface (112) that urges anvil jaw (100) away from cartridge jaw (16), where this reactionary force may be particularly great when firing on thick tissue. The above noted engagement between upper pin (38) and upper guide surfaces (136) of anvil jaw body (110) counteracts this reactionary force and constrains anvil jaw (100) vertically relative to cartridge jaw (16), thereby controlling a size of the tissue gap defined between anvil surface (112) and cartridge deck (72) during firing.128128128128

It will be understood that a thickness of flanges (134) defines a corresponding height of narrow slot portion (130) of anvil slot (122). Additionally, such thickness and height at a given longitudinal location of anvil slot (122) determines the size of the corresponding tissue gap defined between anvil surface (112) and cartridge deck (72) as firing beam (14) reaches that longitudinal location during a firing stroke. Furthermore, the size of the tissue gap at a given longitudinal location defines a corresponding formed height of staple(s) formed at that longitudinal location. As illustrated in FIG. 11 by the parallel relationship between upper guide surface (136) and the longitudinal axis (A) of anvil jaw body (110), each flange (134) of the present example has a uniform thickness (T1) along the length of anvil slot (122), thus providing narrow slot portion (130) with a uniform height along the length of anvil slot (122) and providing upper guide surfaces (136) with a level configuration. Accordingly, anvil jaw (100) is configured to maintain a uniform tissue gap size as firing beam (14) passes distally through anvil slot (122) during a firing stroke, thus providing staples (47) with a uniform formed height along the length of the anvil jaw (100).

B. Exemplary Anvil Jaw Body with Convex Anvil Slot

Figure 12:
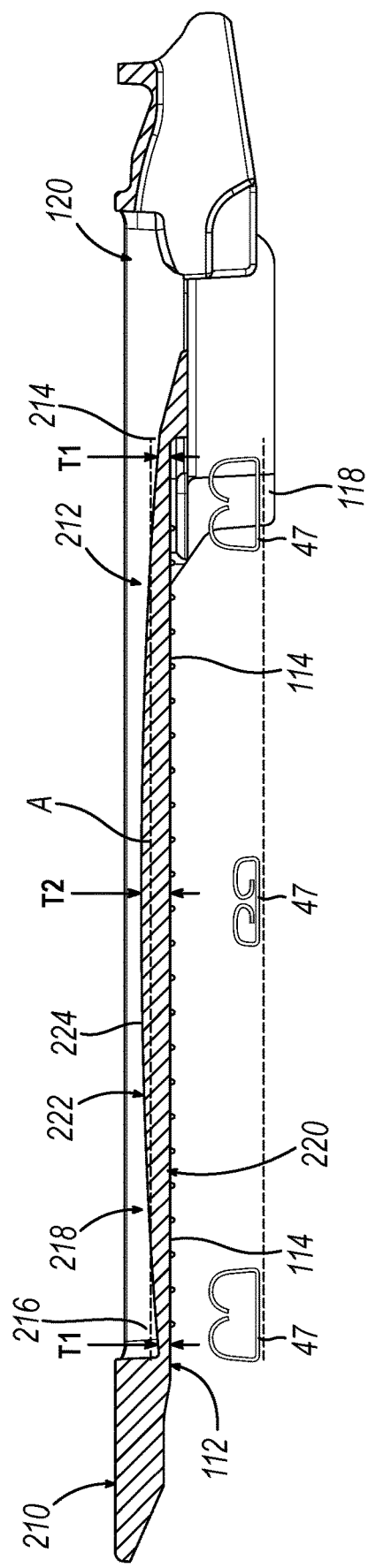
FIG. 12 depicts a cross-sectional side view of another exemplary anvil jaw body, showing a firing member slot flange of the anvil jaw body with a variable thickness that defines a convex flange surface, and schematically showing exemplary staples formable by the anvil jaw body.

FIG. 12 shows another exemplary anvil jaw body (210) that is similar to anvil jaw body (110) described above except as otherwise described below. Like anvil jaw body (110), anvil jaw body (210) includes an elongate anvil slot (212) configured to slidably receive a firing member, such as firing beam (14). Anvil slot (212) extends longitudinally from a proximal slot end (214) at a proximal end of the plurality of staple forming pockets (114) to a distal slot end (216) at a distal end of the plurality of staple forming pockets (114). Additionally, anvil slot (212) includes a wide slot portion (218) and a narrow slot portion (220) that define a pair of elongate flanges (222) each having an upper guide surface (224).

Unlike upper guide surfaces (136) of flanges (134), upper guide surfaces (224) of flanges (222) are convexly curved relative a longitudinal axis (A) of anvil jaw body (210). As shown, a thickness of each flange (222) varies continuously from a minimum thickness (T1) at proximal slot end (214), to a maximum thickness (T2) at a medial location of anvil slot (212), back to the minimum thickness (T1) at distal slot end (216). The height of narrow slot portion (220) varies similarly along the length of anvil slot (212). Accordingly, as upper pin (38) of firing beam (14) advances distally over upper guide surfaces (224) of flanges (222) during a firing stroke, anvil jaw body (210) is permitted a minimal degree of pivotal movement relative to cartridge jaw (16) such that the tissue gap varies in size during the firing stroke. Specifically, anvil jaw body (210) is pivoted closer to cartridge jaw (16) to thereby decrease the tissue gap size as the thickness of flanges (222) increases, and anvil jaw body (210) is permitted to pivot away from cartridge jaw (16) to thereby increase the tissue gap size as the thickness of flanges (222) decreases. Accordingly, in the present example, anvil jaw body (210) is configured to define a maximum tissue gap at each of proximal slot end (214) and distal slot end (216) where flanges (222) have a minimum thickness (T1), and a minimum tissue gap at the medial location of anvil slot (212) where flanges (222) have a maximum thickness (T2).

As noted above, a larger tissue gap yields formed staples (47) with larger formed heights, and a smaller tissue gap yields formed staples (47) with smaller formed heights. Accordingly, in the present example, staples (47) are formed with a maximum formed height at proximal slot end (214) and distal slot end (216), and with a minimum formed height at the medial location of anvil slot (212), with the formed heights of staples varying progressively between proximal and distal slot ends (214, 216). This variation in formed staple height thus renders anvil jaw body (210) suited to stapling on a section of tissue that is thinner at a medial section portion and thicker at end section portions.130130

C. Exemplary Anvil Jaw Body with Concave Anvil Slot

Figure 13:
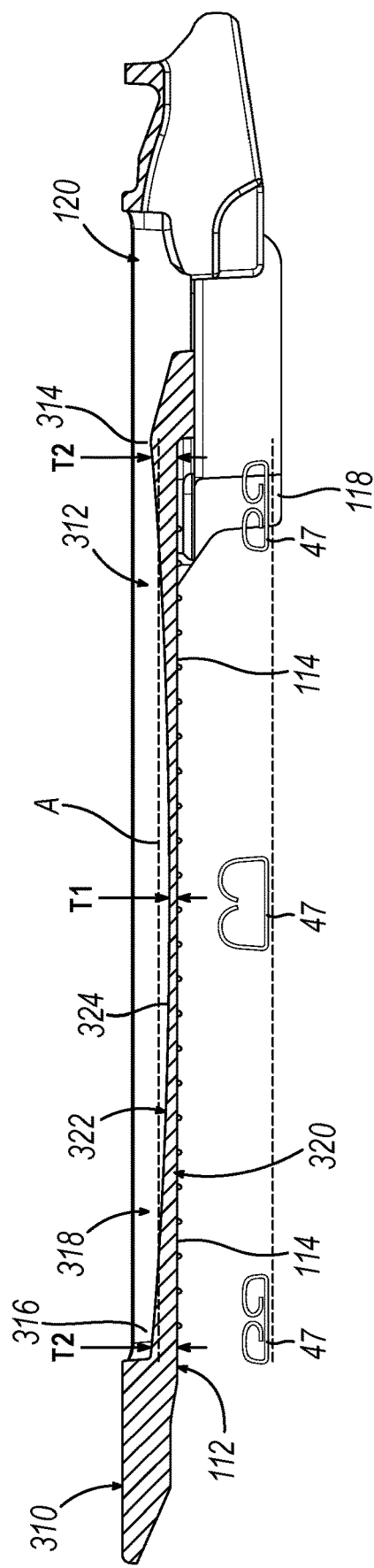
FIG. 13 depicts a cross-sectional side view of another exemplary anvil jaw body, showing a firing member slot flange of the anvil jaw body with a variable thickness that defines a concave flange surface, schematically showing exemplary staples formable by the anvil jaw body.

FIG. 13 shows another exemplary anvil jaw body (310) that is similar to anvil jaw body (210) described above except as otherwise described below. Like anvil jaw body (210), anvil jaw body (310) includes an elongate anvil slot (312) configured to slidably receive a firing member, such as firing beam (14). Anvil slot (312) extends longitudinally from a proximal slot end (314) at a proximal end of the plurality of staple forming pockets (114) to a distal slot end (316) at a distal end of the plurality of staple forming pockets (114). Additionally, anvil slot (312) includes a wide slot portion (318) and a narrow slot portion (320) that define a pair of elongate flanges (322) each having an upper guide surface (324).

Unlike upper guide surfaces (224) of flanges (222), upper guide surfaces (324) of flanges (322) are concavely curved relative a longitudinal axis (A) of anvil jaw body (310). As shown, a thickness of each flange (322) varies continuously from a maximum thickness (T2) at proximal slot end (314), to a minimum thickness (T1) at a medial location of anvil slot (312), back to the maximum thickness (T2) at distal slot end (316). Accordingly, anvil jaw body (310) is configured to define a maximum tissue gap and thus a maximum formed staple height at the medial location of anvil slot (312) where flanges (322) have a minimum thickness (T1). Anvil jaw body (310) is further configured to define a minimum tissue gap and thus a minimum formed staple height at each of proximal slot end (314) and distal slot end (316) where flanges (322) have a maximum thickness (T2). This variation in formed staple height thus renders anvil jaw body (310) suited to stapling on a section of tissue that is thicker at a medial section portion and thinner at end section portions.

D. Exemplary Anvil Jaw Body with Upwardly Angled Anvil Slot

Figure 14:
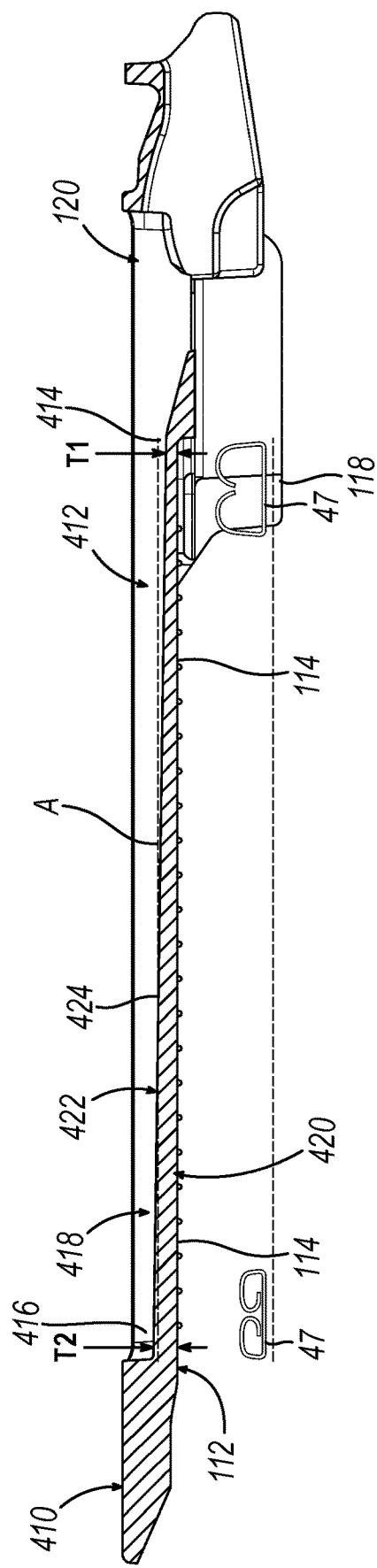
FIG. 14 depicts a cross-sectional side view of another exemplary anvil jaw body, showing a firing member slot flange of the anvil jaw body with a variable thickness that defines an upwardly sloped flange surface, schematically showing exemplary staples formable by the anvil jaw body.

FIG. 14 shows another exemplary anvil jaw body (410) that is similar to anvil jaw bodies (110, 210, 310) described above except as otherwise described below. Like anvil jaw bodies (110, 210, 310), anvil jaw body (410) includes an elongate anvil slot (412) configured to slidably receive a firing member, such as firing beam (14). Anvil slot (412) extends longitudinally from a proximal slot end (414) at a proximal end of the plurality of staple forming pockets (114) to a distal slot end (416) at a distal end of the plurality of staple forming pockets (114). Additionally, anvil slot (412) includes a wide slot portion (418) and a narrow slot portion (420) that define a pair of elongate flanges (422) each having an upper guide surface (424).

Unlike upper guide surfaces (136, 224, 324) of flanges (134, 222, 322), upper guide surfaces (424) of flanges (422) are planar and angled upwardly in a distal direction relative to a longitudinal axis (A) of anvil jaw body (410). As shown, a thickness of each flange (422) varies continuously from a minimum thickness (T1) at proximal slot end (414), to maximum thickness (T2) at distal slot end (416). Accordingly, anvil jaw body (410) is configured to define a maximum tissue gap and thus a maximum formed staple height at proximal slot end (414) where flanges (422) have a minimum thickness (T1). Anvil jaw body (410) is further configured to define a minimum tissue gap and thus a minimum formed staple height at distal slot end (416) where flanges (422) have a maximum thickness (T2). This variation in formed staple height thus renders anvil jaw body (410) suited to stapling on a section of tissue that is thicker at a proximal section end and thinner at a distal section end.

E. Exemplary Anvil Jaw Body with Downwardly Angled Anvil Slot

Figure 15:
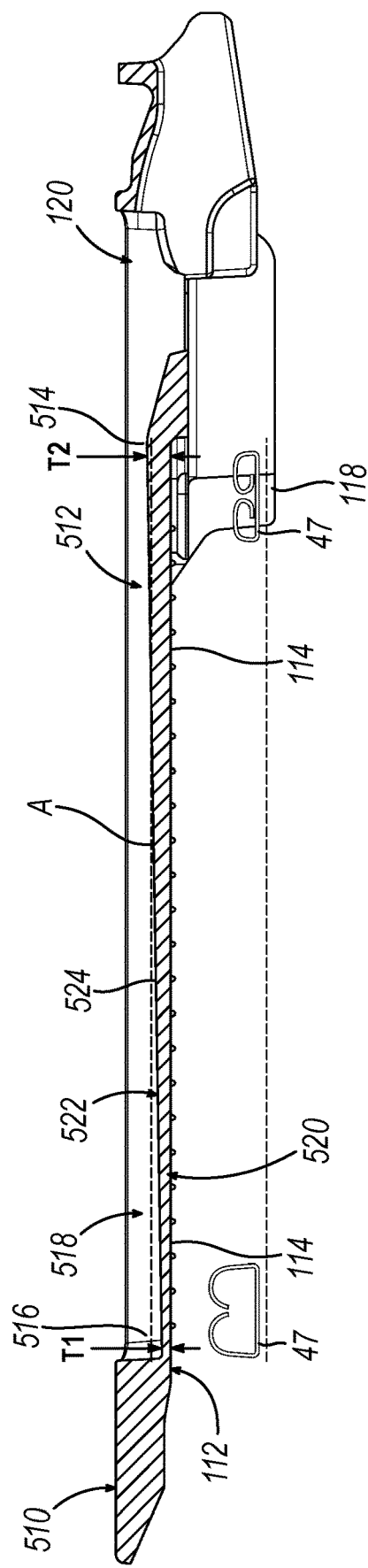
FIG. 15 depicts a cross-sectional side view of another exemplary anvil jaw body, showing a firing member slot flange of the anvil jaw body with a variable thickness that defines a downwardly sloped flange surface, schematically showing exemplary staples formable by the anvil jaw body.

FIG. 15 shows another exemplary anvil jaw body (510) that is similar to anvil jaw body (410) described above except as otherwise described below. Like anvil jaw body (410), anvil jaw body (510) includes an elongate anvil slot (512) configured to slidably receive a firing member, such as firing beam (14). Anvil slot (512) extends longitudinally from a proximal slot end (514) at a proximal end of the plurality of staple forming pockets (114) to a distal slot end (516) at a distal end of the plurality of staple forming pockets (114). Additionally, anvil slot (512) includes a wide slot portion (518) and a narrow slot portion (520) that define a pair of elongate flanges (522) each having an upper guide surface (524).

Unlike upper guide surfaces (424) of flanges (422), upper guide surfaces (524) of flanges (522) are planar and angled downwardly in a distal direction relative to a longitudinal axis (A) of anvil jaw body (510). As shown, a thickness of each flange (522) varies continuously from a maximum thickness (T2) at proximal slot end (514), to minimum thickness (T1) at distal slot end (516). Accordingly, anvil jaw body (410) is configured to define a minimum tissue gap and thus a minimum formed staple height at proximal slot end (514) where flanges (522) have a maximum thickness (T2). Anvil jaw body (510) is further configured to define a maximum tissue gap and thus a maximum formed staple height at distal slot end (516) where flanges (522) have a minimum thickness (T1). This variation in formed staple height thus renders anvil jaw body (510) suited to stapling on a section of tissue that is thinner at a proximal section end and thicker at a distal section end.

F. Exemplary Anvil Jaw Body with Undulating Anvil Slot

Figure 16:
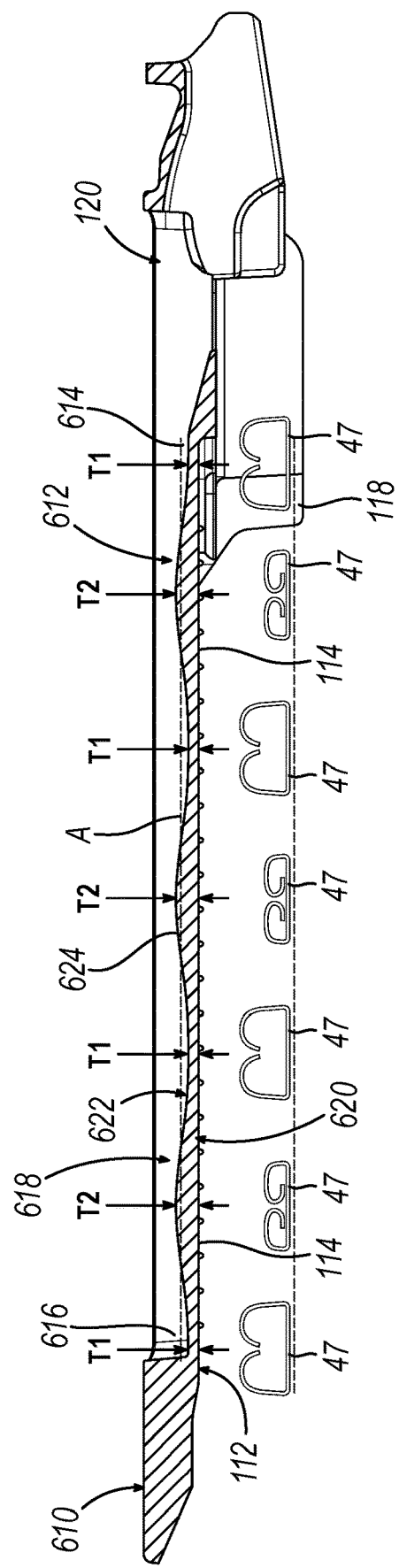
FIG. 16 depicts a cross-sectional side view of another exemplary anvil jaw body, showing a firing member slot flange of the anvil jaw body with a variable thickness that defines an undulating flange surface, schematically showing exemplary staples formable by the anvil jaw body.

FIG. 16 shows another exemplary anvil jaw body (610) that is similar to anvil jaw bodies (110, 210, 310, 410, 510) described above except as otherwise described below. Like anvil jaw bodies (110, 210, 310, 410, 510), anvil jaw body (610) includes an elongate anvil slot (612) configured to slidably receive a firing member, such as firing beam (14). Anvil slot (612) extends longitudinally from a proximal slot end (614) at a proximal end of the plurality of staple forming pockets (114) to a distal slot end (616) at a distal end of the plurality of staple forming pockets (114). Additionally, anvil slot (612) includes a wide slot portion (618) and a narrow slot portion (620) that define a pair of elongate flanges (622) each having an upper guide surface (624).

Unlike upper guide surfaces (136, 224, 324, 424, 524) of flanges (134, 222, 322, 422, 522), upper guide surfaces (624) of flanges (622) undulate uniformly relative to a longitudinal axis (A) of anvil jaw body (610) along the length of anvil slot (612). As shown, a thickness of each flange (622) varies continuously between a minimum thickness (T1) and a maximum thickness (T2) such that each flange (622) includes multiple concave sections defined by minimum thickness (T1) and multiple convex sections defined by maximum thickness (T2). Anvil jaw body (610) is configured to define a maximum tissue gap and thus a maximum formed staple height at the trough of each convex section corresponding to minimum thickness (T1). Anvil jaw body (610) is further configured to define a minimum tissue gap and thus a minimum formed staple height at the peak of each concave section corresponding to maximum thickness (T2). This variation in formed staple height thus renders anvil jaw body (610) suited to stapling on a section of tissue that includes portions of alternating thickness.

III. Exemplary Anvil Jaw Body with Variable-Width Anvil Slot

As described above, anvil jaw (18) is hinged to the remaining portion of end effector (12) at the proximal end of anvil jaw (18). This hinged connection can allow anvil jaw (18) to pivot laterally, about a vertical axis, relative to lower jaw (16) just slightly such that the distal ends of jaws (16, 18) may become misaligned laterally, creating lateral misalignment between staples (47) and staple forming pockets (53) that risks malformation of staples (47). As discussed above in connection with anvil jaw (100), narrow slot portion (130) can provide some constraint of lateral movement of anvil jaw (100) relative to lower cartridge jaw (16) via engagement between firing beam (14), which itself is constrained laterally relative to cartridge jaw (16) via cartridge slot (49), and side guide surfaces (138) of anvil jaw body flanges (134), seen best in FIG. 10. This lateral constraint is in addition to lateral constraint provided by the interface between tissue stops (118) of anvil jaw (100) and lateral side surfaces of cartridge jaw (16). While this lateral constraint may prove effective to ensure lateral alignment of jaws (16, 100) at their proximal ends, it may still be desirable to provide an additional feature that promotes lateral alignment of jaws (16, 100) at their distal ends.

Figure 17:
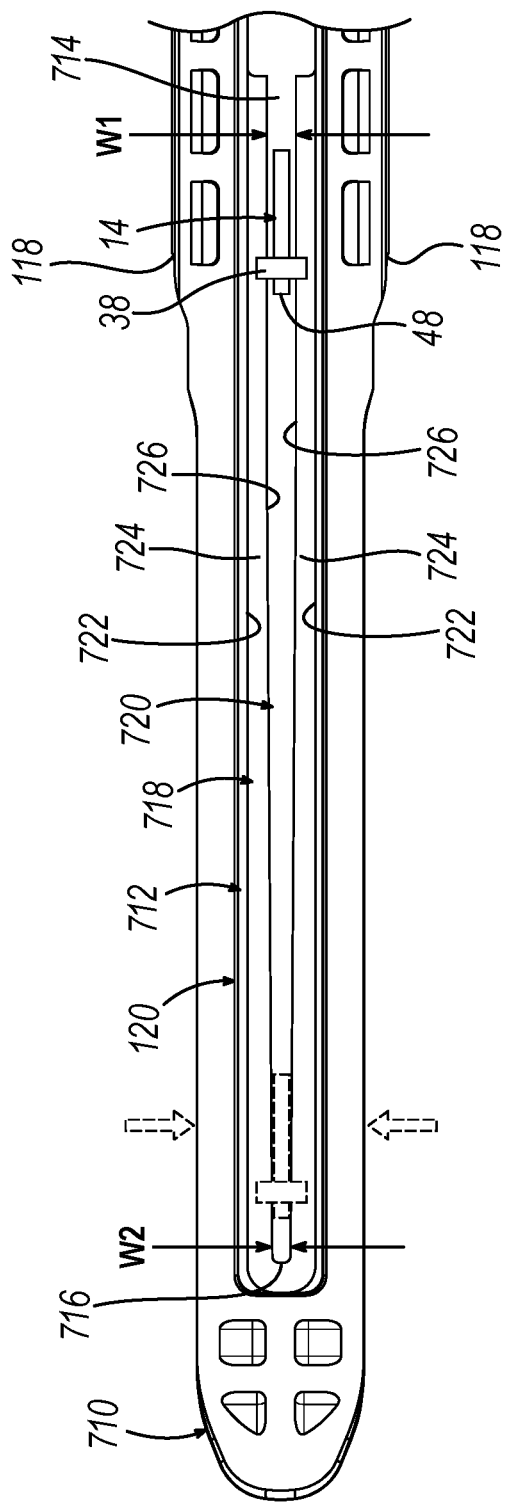
FIG. 17 depicts an elevational top view of another exemplary anvil jaw body and a firing member positioned in a firing member slot of the anvil jaw body, showing the firing member slot having a variable width.

FIG. 17 shows another exemplary anvil jaw body (710) that is similar to anvil jaw bodies (110, 210, 310, 410, 510, 610) described above except as otherwise described below. Like anvil jaw bodies (110, 210, 310, 410, 510, 610), anvil jaw body (710) includes an elongate anvil slot (712) configured to slidably receive a firing member, such as firing beam (14). Anvil slot (712) extends longitudinally from a proximal slot end (714) at a proximal end of the plurality of staple forming pockets (114) to a distal slot end (716) at a distal end of the plurality of staple forming pockets (114). Additionally, anvil slot (712) includes a wide slot portion (718) and a narrow slot portion (720) that define a pair of elongate flanges (722) each having an upper guide surface (724) and a side guide surface (726).

Unlike narrow slot portions (130, 220, 320, 420, 520, 620), narrow slot portion (720) of anvil slot (712) has a transverse width that varies along the length of anvil slot (712). Specifically, the width transitions from a maximum slot width (W1) at proximal slot end (714) to a minimum slot width (W2) at distal slot end (716). In the present example, narrow slot portion (720) tapers uniformly from maximum slot width (W1) to minimum slot width (T2) along at least a medial portion of anvil slot (712) between proximal and distal slot ends (714, 716). As shown, as the width of narrow slot portion (720) decreases, a width of each flange (722) increases, such that each flange (722) has a minimum flange width at proximal slot end (714) corresponding to maximum slot width (W1) and a maximum flange width at distal slot end (716) corresponding to minimum slot width (W2). Additionally, as shown, maximum slot width (W1) may be sized notably larger than a width of firing beam (14) at proximal slot end (714), and minimum slot width (W2) may be sized closer to, though still slightly larger than, the width of firing beam (14) with a degree of tolerance suitable to permit relative translation of firing beam (14) without binding at distal slot end (716). Accordingly, as firing beam (14) advances distally from proximal slot end (714) to distal slot end (716), firing beam (14) may progressively engage side guide surfaces (726) of flanges (722) to draw anvil jaw body (710) increasingly into lateral alignment with cartridge jaw (16), thereby increasingly constraining any lateral pivoting of anvil jaw body (710) to promote proper staple engagement with the staple forming pockets (114) at the distal end of end effector (12).

It will be appreciated that the variable-slot-width configuration of anvil jaw body (710) may be combined with the variable-slot-height configuration of any of the other anvil jaw bodies (210, 310, 310, 410, 510, 610) disclosed herein. As an example, the features of variable-width anvil slot (712) may be used in combination with undulating anvil slot (612) of FIG. 16 described above.

IV. Exemplary Method of Making an Anvil Jaw

Figure 18:
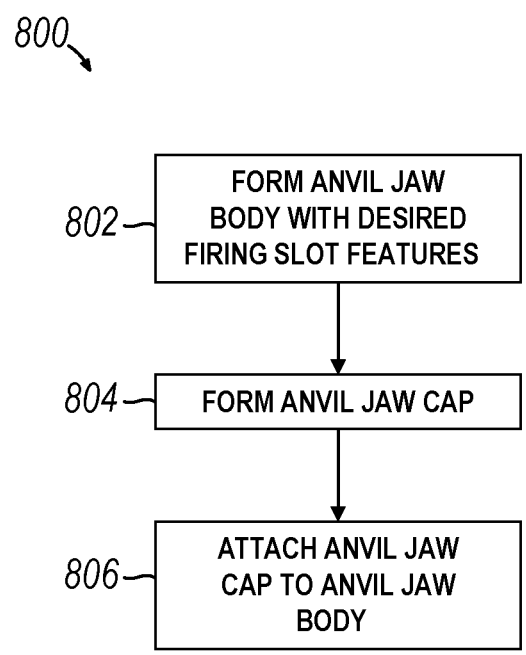
FIG. 18 depicts a diagrammatic view of an exemplary method for forming an anvil jaw having an anvil jaw body and an anvil jaw cap.

FIG. 18 shows an exemplary method (800) that may be employed to form an anvil jaw that includes an anvil jaw cap, such as anvil jaw cap (102) described above or variations thereof, and an anvil jaw body, such as any of anvil jaw bodies (110, 210, 310, 410, 510, 610, 710) described above or variations thereof.

At first step (802) of method (800), the anvil jaw body is formed using one or more suitable manufacturing methods, such as liquid injection molding. The staple forming pockets of the anvil jaw body may be formed concurrently with the formation of the anvil jaw body, for example during a molding procedure, or subsequently, for example via a coining procedure. At step (804), the anvil jaw cap is formed separately from the anvil jaw body using one or more suitable manufacturing methods, such as liquid injection molding. It will be appreciated that forming the anvil jaw body with an elongate opening similar to elongate opening (120) described above enables formation of an anvil slot having a unique geometry with one or more dimensions that varies along a length of the anvil slot, for example as described above. Additionally, it will be appreciated that steps (802, 804) may be performed in any desired order or simultaneously. After completion of steps (802, 804), at step (806) the anvil jaw cap is securely attached to the anvil jaw body within its elongate opening, for example as seen in FIGS. 8-10 in connection with anvil jaw (100). Such attachment may be achieved by welding, compression fit, adhesive attachment, releasable mechanical attachment, or various other methods that will be readily apparent to those of ordinary skill in the art in view of the teachings herein. Additionally, attachment of the anvil jaw cap to the anvil jaw body may be effective to increase a rigidity of the anvil jaw body and to inhibit fluids from entering the anvil jaw slot through the elongate opening during a surgical procedure.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a jaw body, wherein a proximal end of the jaw body is configured to couple with an end effector portion of a surgical stapler such that the jaw body is configured to cooperate with an opposing jaw of the surgical stapler to compress, staple, and cut tissue; (b) an anvil surface defined by the jaw body and having a plurality of staple forming pockets configured to form a plurality of staples ejected by a stapling assembly of the surgical stapler; and (c) an elongate slot extending through the anvil surface and along a longitudinal axis of the jaw body from a proximal slot end at a proximal end of the plurality of staple forming pockets to a distal slot end at a distal end of the plurality of staple forming pockets, wherein the elongate slot comprises a first slot portion configured to slidably receive a first portion of a firing member of the surgical stapler, and a second slot portion that opens to the anvil surface and is configured to slidably receive a second portion of the firing member, wherein the first slot portion is wider than the second slot portion in a direction transverse to the longitudinal axis, and wherein a dimension of the second slot portion varies along the longitudinal axis between the proximal slot end and the distal slot end.

Example 2

The apparatus of Example 1, wherein a width of the second slot portion varies along a length of the elongate slot between the proximal and distal slot ends.

Example 3

The apparatus of Example 3, wherein the width of the second slot portion is larger at the proximal slot end than at the distal slot end.

Example 4

The apparatus of any of Examples 2 through 3, wherein the width of the second slot portion tapers along at least a medial portion of the elongate slot between the proximal slot end and the distal slot end.

Example 5

The apparatus of any of the preceding Examples, wherein a height of the second slot portion varies along a length of the elongate slot between the proximal and distal slot ends.

Example 6

The apparatus of any of Example 5, wherein the jaw body includes a pair of elongate flanges that cooperate to define the anvil surface and are spaced apart from one another to define the second slot portion, wherein a thickness of the flanges defines the height of the second slot portion.

Example 7

The apparatus of any of Examples 5 through 6, wherein the height of the second slot portion is smaller at the proximal slot end than at the distal slot end.

Example 8

The apparatus of any of Examples 5 through 7, wherein the height of the second slot portion increases continuously from the proximal slot end to the distal slot end.

Example 9

The apparatus of Example 5, wherein the height of the second slot portion is larger at the proximal slot end than at the distal slot end.

Example 10

The apparatus of Example 9, wherein the height of the second slot portion decreases continuously from the proximal slot end to the distal slot end.

Example 11

The apparatus of any of Examples 5 through 10, wherein the second slot portion exhibits at least one transition along the longitudinal axis from an increasing height to decreasing height.

Example 12

The apparatus of Example 11, wherein the at least one transition is located along a medial section of the elongate slot.

Example 13

The apparatus of any of Examples 11 through 12, wherein the at least one transition includes a plurality of transitions located between the proximal slot end and the distal slot end.

Example 14

The apparatus of any of the preceding Examples, wherein the jaw body includes a first side that defines the anvil surface and a second side that includes an elongate opening that communicates with the elongate slot.

Example 15

The apparatus of Example 14, further comprising a cap affixed to the second side of the jaw body such that the cap covers the elongate opening and encloses the elongate slot.

Example 16

An apparatus, comprising: (a) a jaw body, wherein a proximal end of the jaw body is configured to couple with an end effector portion of a surgical stapler such that the jaw body is configured to cooperate with an opposing jaw of the surgical stapler to compress, staple, and cut tissue; (b) an anvil surface defined by the jaw body and having a plurality of staple forming pockets configured to form a plurality of staples ejected by a stapling assembly of the surgical stapler; and (c) an elongate slot extending through the anvil surface and along a longitudinal axis of the jaw body from a proximal slot end at a proximal end of the plurality of staple forming pockets to a distal slot end at a distal end of the plurality of staple forming pockets, wherein the elongate slot defines a pair of elongate guide features of the jaw body that extend along the longitudinal axis from the proximal slot end to the distal slot end, wherein the elongate slot is configured to slidably receive a firing member of the surgical stapler between the elongate guide features, wherein a dimension of each elongate guide feature varies along the longitudinal axis between the proximal slot end and the distal slot end such that the elongate guide features are configured to at least one of allow for a variable distance between the anvil surface and the opposing jaw or promote lateral alignment between the anvil surface and the opposing jaw as the firing member advances distally along the elongate slot.

Example 17

The apparatus of Example 16, wherein a thickness of each elongate guide feature varies along the longitudinal axis between the proximal slot end and the distal slot end such that the elongate guide features are configured to allow for a variable distance between the anvil surface and the opposing jaw as the firing member advances distally along the elongate slot.

Example 18

The apparatus of any of Examples 16 through 17, wherein a width of each elongate guide feature increases distally from the proximal slot end to the distal slot end such that the elongate guide features are configured to promote lateral alignment between the anvil surface and the opposing jaw as the firing member advances distally along the elongate slot.

Example 19

A method of forming an anvil jaw configured for use with a surgical stapler, the method comprising: (a) forming a jaw body of the anvil jaw such that: (i) a first side of the jaw body includes an elongate opening, and (ii) a second side of the jaw body includes: (A) an anvil surface having a plurality of staple forming pockets configured to form a plurality of staples ejected by a stapling assembly of the surgical stapler, and (B) an elongate slot extending along through the anvil surface in a direction toward the first side such that the elongate slot communicates with the elongate opening, wherein the elongate slot is configured to slidably receive a firing member of the surgical stapler; and (b) affixing a cap to the first side of the jaw body such that the cap covers the elongate opening and encloses the elongate slot.

Example 20

The surgical instrument of Example 19, wherein the elongate slot extends along a longitudinal axis of the jaw body between a proximal slot end at a proximal end of the plurality of staple forming pockets and a distal slot end at a distal end of the plurality of staple forming pockets, wherein forming the jaw body of the anvil jaw includes forming the jaw body with a pair of elongate flanges that extend along the longitudinal axis and define at least a portion of the elongate slot, wherein at least one of a thickness or a width of each elongate flange varies between the proximal slot end and the distal slot end.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a jaw body, wherein a proximal end of the jaw body is configured to couple with an end effector portion of a surgical stapler such that the jaw body is configured to cooperate with an opposing jaw of the surgical stapler to compress, staple, and cut tissue;
   (b) an anvil surface defined by the jaw body and having a plurality of staple forming pockets configured to form a plurality of staples ejected by a stapling assembly of the surgical stapler; and
   (c) an elongate slot extending through the anvil surface and along a longitudinal axis of the jaw body from a proximal slot end at a proximal end of the plurality of staple forming pockets to a distal slot end at a distal end of the plurality of staple forming pockets,
   wherein the elongate slot comprises a first slot portion configured to slidably receive a first portion of a firing member of the surgical stapler, and a second slot portion that opens to the anvil surface and is configured to slidably receive a second portion of the firing member,
   wherein the first slot portion is wider than the second slot portion in a direction transverse to the longitudinal axis, and
   wherein a dimension of the second slot portion varies continuously along the longitudinal axis between the proximal slot end and the distal slot end such that the second slot portion is configured to promote movement of the jaw body relative to the opposing jaw in response to distal advancement of the firing member through the elongate slot during a firing stroke.

2. The apparatus of claim 1, wherein a width of the second slot portion varies along a length of the elongate slot between the proximal and distal slot ends.

3. The apparatus of claim 2, wherein the width of the second slot portion is larger at the proximal slot end than at the distal slot end.

4. The apparatus of claim 3, wherein the width of the second slot portion tapers along at least a medial portion of the elongate slot between the proximal slot end and the distal slot end.

5. The apparatus of claim 1, wherein a height of the second slot portion varies along a length of the elongate slot between the proximal and distal slot ends.

6. The apparatus of claim 5, wherein the jaw body includes a pair of elongate flanges that cooperate to define the anvil surface and are spaced apart from one another to define the second slot portion, wherein a thickness of the flanges defines the height of the second slot portion.

7. The apparatus of claim 5, wherein the height of the second slot portion is smaller at the proximal slot end than at the distal slot end.

8. The apparatus of claim 7, wherein the height of the second slot portion increases continuously from the proximal slot end to the distal slot end.

9. The apparatus of claim 5, wherein the height of the second slot portion is larger at the proximal slot end than at the distal slot end.

10. The apparatus of claim 9, wherein the height of the second slot portion decreases continuously from the proximal slot end to the distal slot end.

11. The apparatus of claim 5, wherein the second slot portion exhibits at least one transition along the longitudinal axis from an increasing height to decreasing height.

12. The apparatus of claim 11, wherein the at least one transition is located along a medial section of the elongate slot.

13. The apparatus of claim 11, wherein the at least one transition includes a plurality of transitions located between the proximal slot end and the distal slot end.

14. The apparatus of claim 1, wherein the jaw body includes a first side that defines the anvil surface and a second side that includes an elongate opening that communicates with the elongate slot.

15. The apparatus of claim 14, further comprising a cap affixed to the second side of the jaw body such that the cap covers the elongate opening and encloses the elongate slot.

16. An apparatus, comprising:
    (a) a jaw body, wherein a proximal end of the jaw body is configured to couple with an end effector portion of a surgical stapler such that the jaw body is configured to cooperate with an opposing jaw of the surgical stapler to compress, staple, and cut tissue;
    (b) an anvil surface defined by the jaw body and having a plurality of staple forming pockets configured to form a plurality of staples ejected by a stapling assembly of the surgical stapler; and
    (c) an elongate slot extending through the anvil surface and along a longitudinal axis of the jaw body from a proximal slot end at a proximal end of the plurality of staple forming pockets to a distal slot end at a distal end of the plurality of staple forming pockets,
    wherein the elongate slot comprises a first slot portion configured to slidably receive a first portion of a firing member of the surgical stapler, and a second slot portion that opens to the anvil surface and is configured to slidably receive a second portion of the firing member,
    wherein the first slot portion is wider than the second slot portion in a direction transverse to the longitudinal axis, and
    wherein a dimension of the second slot portion varies continuously along the longitudinal axis between the proximal slot end and the distal slot end.

17. The apparatus of claim 16, wherein a width of the second slot portion varies along a length of the elongate slot between the proximal and distal slot ends.

18. The apparatus of claim 16, wherein a height of the second slot portion varies along a length of the elongate slot between the proximal and distal slot ends.

19. The apparatus of claim 16, wherein the jaw body includes a first side that defines the anvil surface and a second side that includes an elongate opening that communicates with the elongate slot.

20. An apparatus, comprising:
(a) a jaw body, wherein a proximal end of the jaw body is configured to couple with an end effector portion of a surgical stapler such that the jaw body is configured to cooperate with an opposing jaw of the surgical stapler to compress, staple, and cut tissue;
(b) an anvil surface defined by the jaw body and having a plurality of staple forming pockets configured to form a plurality of staples ejected by a stapling assembly of the surgical stapler; and
(c) an elongate slot extending through the anvil surface and along a longitudinal axis of the jaw body from a proximal slot end at a proximal end of the plurality of staple forming pockets to a distal slot end at a distal end of the plurality of staple forming pockets,
wherein the elongate slot comprises a first slot portion configured to slidably receive a first portion of a firing driver of the surgical stapler, and a second slot portion that opens to the anvil surface and is configured to slidably receive a second portion of the firing driver,
wherein the first slot portion is wider than the second slot portion in a direction parallel to the anvil surface, and
wherein a dimension of the second slot portion varies continuously along the longitudinal axis between the proximal slot end and the distal slot end.

* * * * *